United States Patent [19]

Chabannes et al.

[11] 4,012,145
[45] Mar. 15, 1977

[54] SPECTROSCOPIC ANALYSIS APPARATUS EMPLOYING MEASUREMENT AND REFERENCE RADIATION

[75] Inventors: Francois Marie Maurice Chabannes, Paris; Edouard Sylvain Milot, Boulogne; Pierre Raymond Louis Godfrin, Suresnes; Pierre Philippe Louis Mailly, Villejuif, all of France

[73] Assignee: Etat Francais, France

[22] Filed: Sept. 6, 1974

[21] Appl. No.: 503,759

[30] Foreign Application Priority Data

Sept. 20, 1973 France ............................ 73.33695

[52] U.S. Cl. ................................. 356/88; 356/93; 356/96; 356/100

[51] Int. Cl.[2] ........................................ G01J 3/42

[58] Field of Search ............... 356/88, 93, 95, 96, 356/97, 100; 250/339, 345, 565

[56] References Cited

UNITED STATES PATENTS

| 3,561,872 | 2/1971 | Grabowski et al. | 356/88 |
|---|---|---|---|
| 3,603,690 | 9/1971 | Hard | 356/209 |
| 3,676,004 | 7/1972 | Prugger et al. | 356/97 |
| 3,790,290 | 2/1974 | Muller et al. | 356/206 |
| 3,843,258 | 10/1974 | Shupe | 356/88 |

FOREIGN PATENTS OR APPLICATIONS 984,590   2/1965   United Kingdom ............. 331/94.5

Primary Examiner—Vincent P. McGraw
Attorney, Agent, or Firm—Larson, Taylor and Hinds

[57] ABSTRACT

The apparatus comprises a coherent radiation source which emits, in succession, respective ones of a plurality of different wavelengths. The emitted radiation is separated into a reference portion and a measurement portion. The measurement portion propagates through a medium such as the atmosphere to be analyzed and is received by a measurement detector. The reference portion is received directly by a reference detector. A processing circuit processes signals representing the portions, produced by the detectors to produce numerical data relating to the spectral analysis of the medium.

23 Claims, 10 Drawing Figures

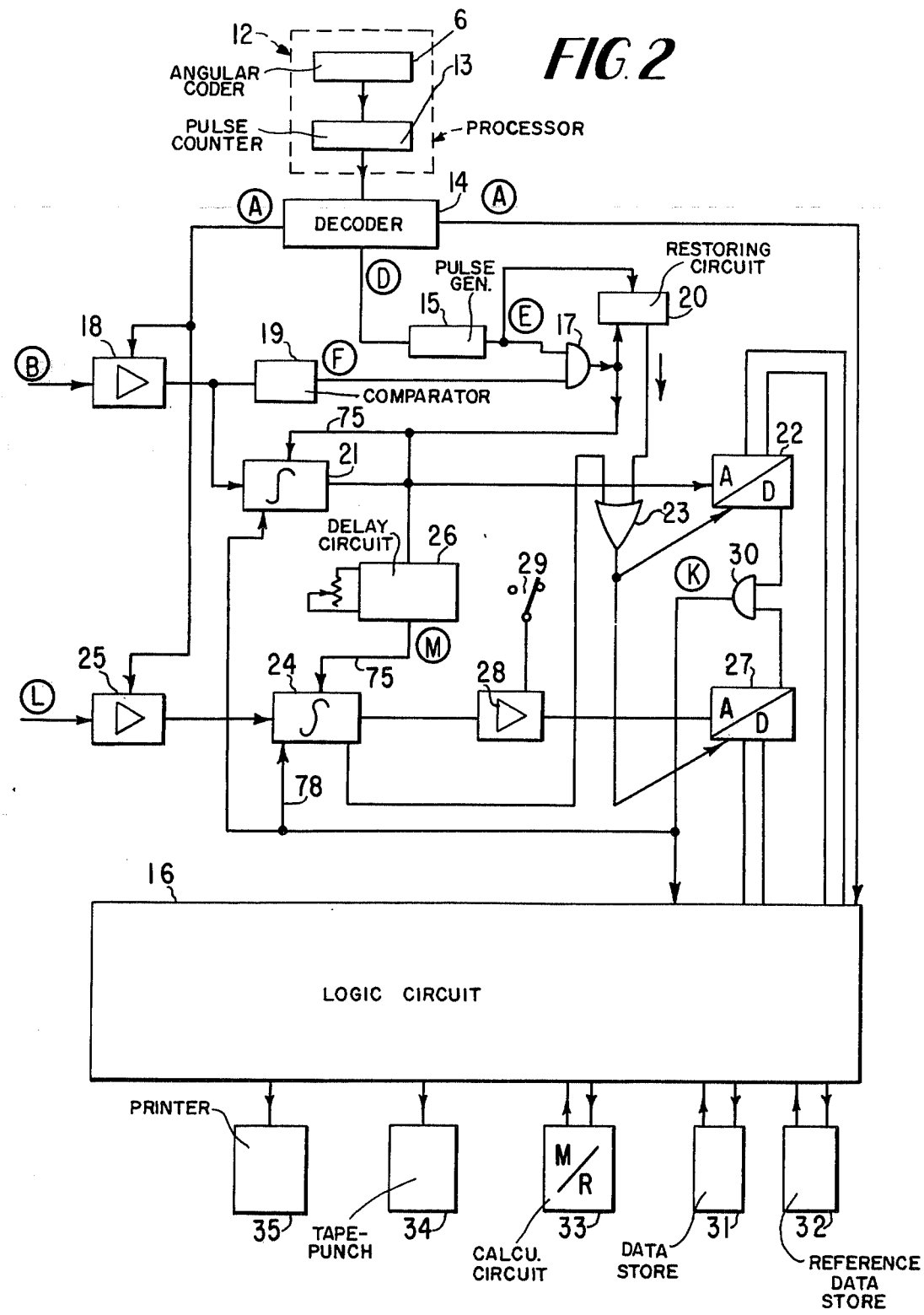

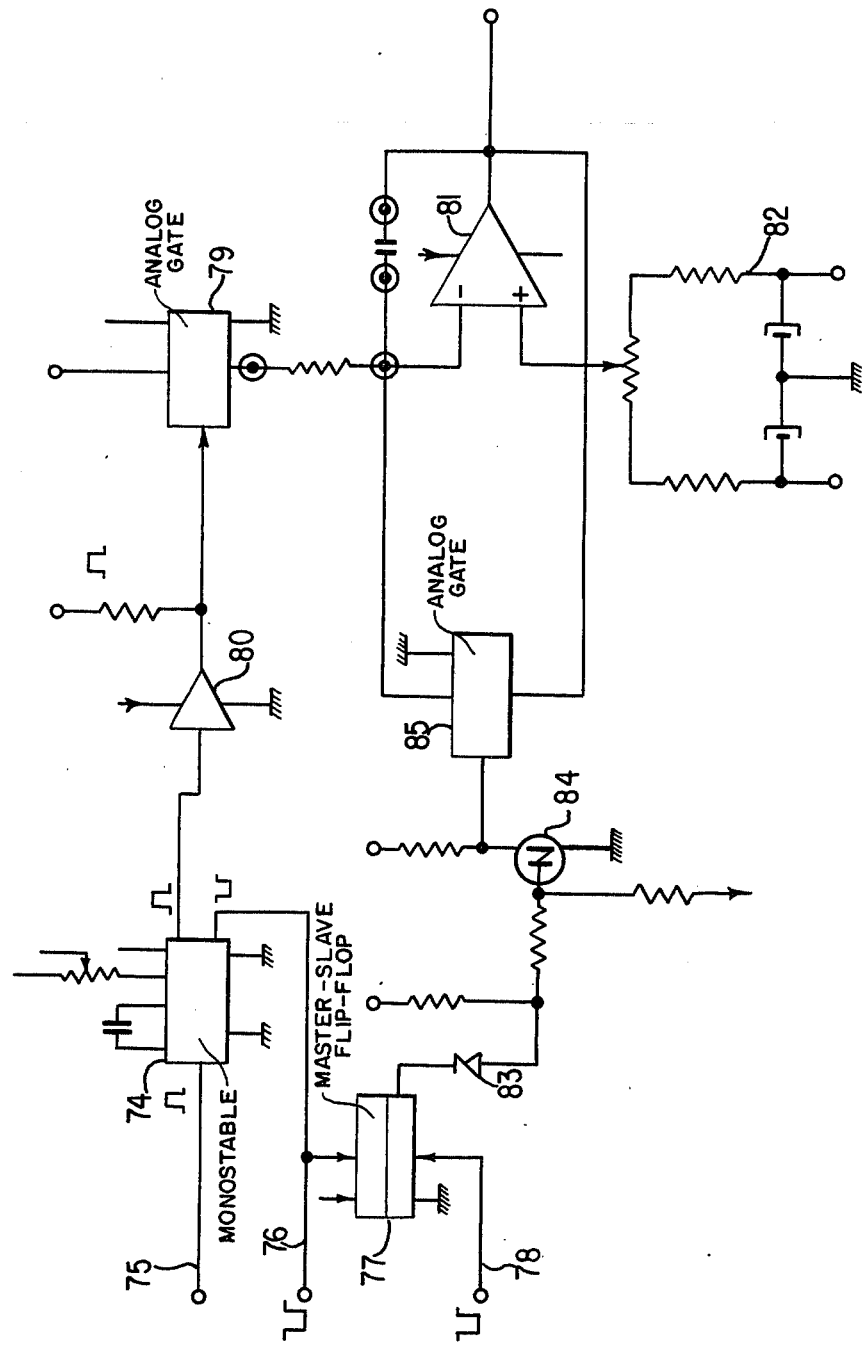

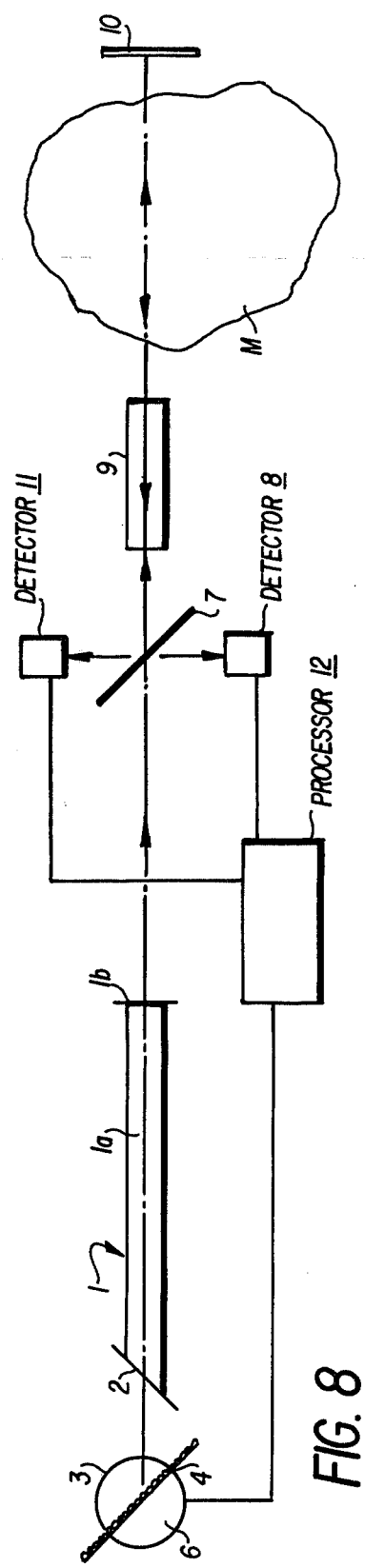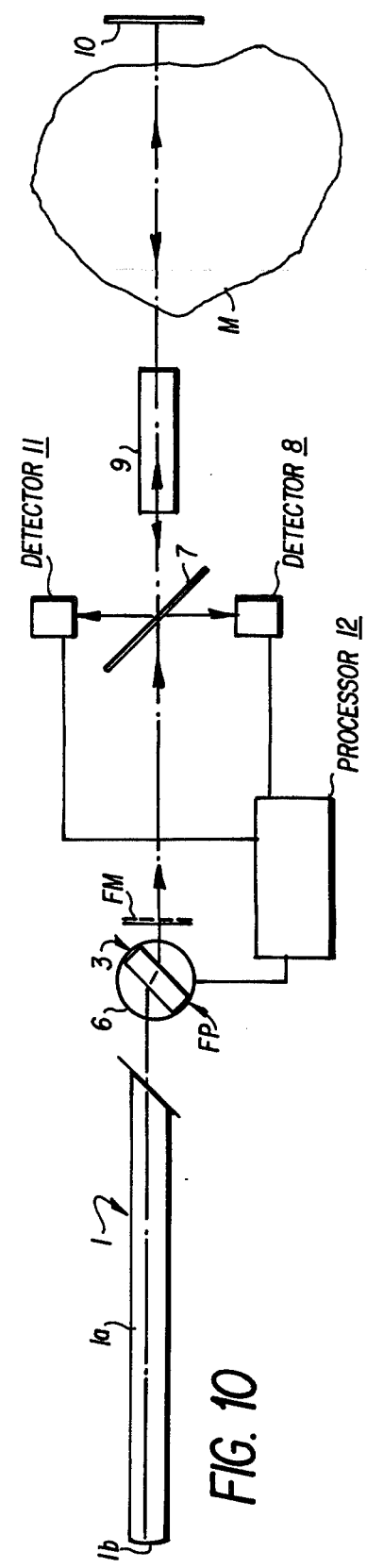

SPECTROSCOPIC ANALYSIS APPARATUS EMPLOYING MEASUREMENT AND REFERENCE RADIATION

BACKGROUND OF THE INVENTION

1. Field of Invention

The present invention relates apparatus for the spectroscopic analysis of a sample of material for determining the chemical composition of the sample. A particular application of the apparatus may be to spectroscopic analysis of a zone of the atmosphere, with a view to evaluating atmosphere pollution.

2. Description of Prior Art

Spectroscopic analysis of a sample can be carried out by analysing the absorption spectrum or the Raman spectrum of the sample.

Apparatus for such analysis generally necessitate sampling and the measures carried into effect on the said sample do not make it possible to follow the evolution of the composition of the medium from which the said sample has been taken.

Spectroscopic analysis apparatus are known which do permit the recording of the luminous phenomena emission spectrum making it possible to follow the evolution of such a spectrum, but the field of application of these apparatus is limited solely to highly luminous elements.

Recently developed apparatus utilise extremely high power lasers by means of which the Raman retrodiffusion or back scattering may be studied for analysing the sample. These apparatus are intended to perform the same functions as the apparatus according to the invention but they have the disadvantage that they necessitate extremely large installations and that they are relatively dangerous due to the high power of the laser beam which is used.

It is a characteristic of these apparatus, that analysis of a sample is performed utilising the Raman spectrum.

Analysis apparatus are known which measure the absorption of a medium on an extremely small number of emitted wavelengths. These apparatus, however, do not permit the analysis of complex mixtures and modification of these apparatus in respect of the selection of wavelengths is difficult.

SUMMARY OF THE INVENTION

It is an object of the invention to remedy the disadvantages encountered in known apparatus, by providing an apparatus for analysing the composition of a medium of considerable thickness, which apparatus, whilst being relatively simple in construction, makes it possible to follow, substantially during the actual time involved, the evolution of the composition of the said medium.

Another object of the invention is to provide an analysis apparatus which is capable of determining, at uniform intervals of time, the absorptions of a sample of a medium on the path of a coherent light beam, of a plurality of predetermined wavelengths, in such manner as to obtain absorption spectra at closely spaced instants of time, such spectra being utilised for determining the composition of the medium through which the beam passes.

The apparatus in accordance with the invention comprises apparatus for the spectroscopic analysis of a sample of material for determining the chemical composition of the sample, the apparatus comprising:

a coherent radiation source for producing, in succession, respective ones of a plurality of different wavelengths of the coherent radiation, the source having an active material from which there can be produced the said different wavelengths of coherent radiation, reflecting means for reflecting radiation in the source, and a wavelength selecting means operable by variation of its angular orientation relative to the axis of propagation of coherent radiation in the source to sequentially select respective ones of the different wavelengths;

a separator for separating the radiation into a measurement portion for irradiating a sample of material and a reference portion;

a reference detector arranged to receive the reference portion and to produce a reference signal representing the reference portion;

a measurement detector arranged to receive the radiation from the sample of material due to the irradiation of the sample by the measurement portion and to produce a measurement signal representing the said radiation from the sample; and a processing circuit for processing the reference and measurement signals in dependence upon variation of the said angular orientation of the selecting means to produce numerical data relating to the spectral analysis of the sample.

BRIEF DESCRIPTION OF THE DRAWINGS

For a better understanding of the invention, and to show how the same may be carried into effect, reference will now be made, by way of example, to the accompanying drawings, in which:

FIG. 2 is a block diagram of an electronic processing circuit of the analysis apparatus of FIG. 1;

FIG. 7 is a circuit diagram of measurement and reference integrators of the processing circuit of FIG. 2;

FIG. 8 is a block diagram similar to that of FIG. 1 illustrating an alternative embodiment of the coherent radiation source 1;

FIG. 10 is a block diagram similar to that of FIG. 1 illustrating yet another embodiment of the invention.

DETAILED DESCRIPTION OF THE INVENTION

Figure 1:
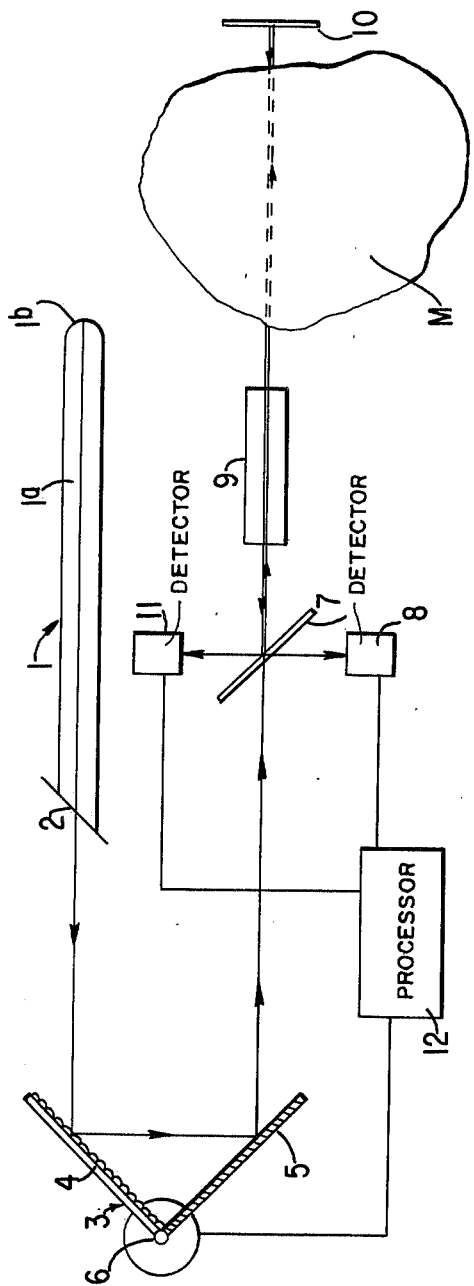
FIG. 1 is a diagram of an analysis apparatus according to the invention.

Referring first of all to FIG. 1, the analysis apparatus according to the inventin comprises a source of coherent radiation 1. The source 1 is arranged to emit light at a plurality of wavelengths. The source has an amplifier medium 1a confined in a tube closed at one end by a reflecting means constituted by a fixed mirror 1b and at the other end by an outlet window 2. The amplifier medium or active material 1a may have a gain curve of several discrete lines or may have only a single extremely wide line or band of wavelengths. Disposed before the outlet window 2 of the tube is a wavelength selecting means comprising a dihedral arrangement 3 of a diffraction grating 4 and a plane reflector 5. An electric motor is provided for rotating the dihedral arrangement. An angular coder 6 is associated with the motor and is adapted to supply to an electronic processing circuit 12 of the analysis device, words representing successive angular positions of the grating 4 of the dihedral arrangement relative to the optical axis of the laser 1, and consequently relating to the wavelengths of light transmitted from the grating 4.

Preferably the source 1 constitutes a $CO_2$ laser which is permanently excited. As an alternative to a $CO_2$ laser, it is possible to employ gaseous mixture lasers of all types, in particular isotope mixture lasers.

It is also possible to employ lasers other than molecular lasers, for example liquid lasers which emit only a single extremely wide line or band of wavelengths. In such a case the laser 1 then emits a single relatively long pulse and the wavelength of light reflected from the refractor varies with angular position of the grating 4 relative to the optical axis of the laser. Pumping may be effected either continuously or by pulses, and may be synchronised with rotation of the grid.

The fixed mirror 1b may be partially transparent, and the laser arranged so that emission takes place through it. This embodiment is illustrated in FIG. 8.

Figure 9:
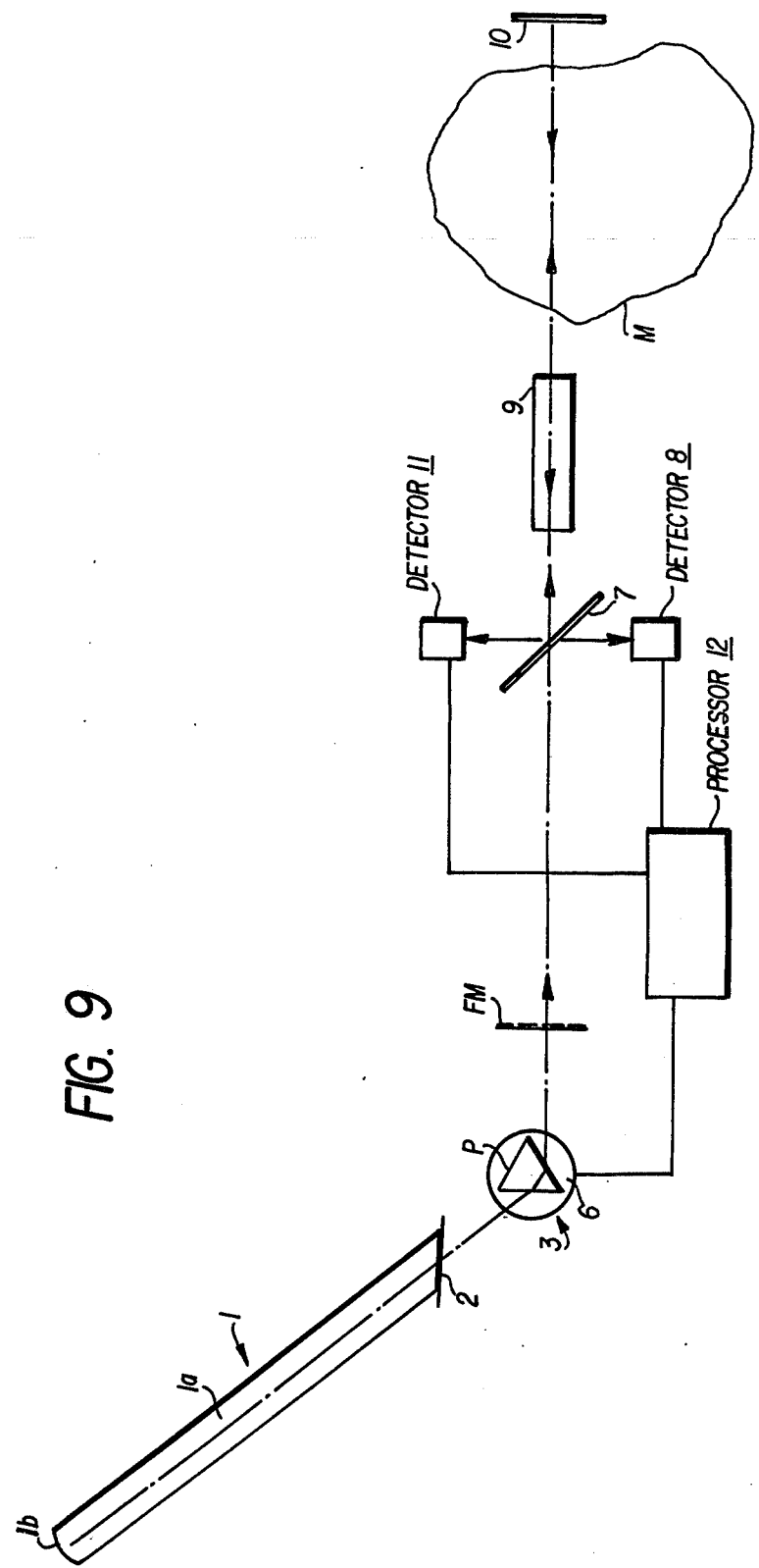
FIG. 9 is a block diagram similar to that in FIG. 1 illustrating a further embodiment of the invention.

Alternatively, the dihedral arrangement shown in FIG. 1, may be replaced by another reflector defining with the mirror 1b a laser cavity, a rotatable prism being disposed in the cavity. In such a case as illustrated in FIG. 9, the other reflector which may be a fixed mirror FM defines with the fixed mirror 1b the ends of a cavity in which is disposed a rotatably arranged prism P. In this case, the emission may be effected through any optional one of the fixed mirrors. In the embodiment of FIG. 10 the prism is replaced with a rotatable Fabry-Perot system.

It should be noted that the cavity defined between the two fixed mirrors or by the one fixed mirrow 1b and the rotatable grating 4 should be sufficiently long that, at all times, one mode at least of the cavity thus formed has a frequency equal to or falling within the bandwidth of a line of the amplifier medium or active material 1a.

For detecting orientation of the grating, a laser beam and detectors may be employed instead of the angular coder 6.

Disposed to be on the path of the beam of light emitted by the source 1 is a separator 7 for splitting the emitted beam into a reference portion and a measurement portion. The reference portion of the beam serves as reference beam and is directed towards a reference detector 8 for producing a reference signal representing the particular line or wavelength being transmitted at any particular moment, whereas the other measurement portion of the beam serving as a measurement beam is emitted towards the medium M to be studied, for example a zone of the atmosphere, through intermediary of an emission-reception telescope or collimator 9 for rendering the emitted beam less divergent. The collimator also recovers the greater portion of the light reflected from a reflector 10 disposed, at predetermined distance from the separator 7, in such manner as to reflect the measurement beam along a path identical with the incident path. A measurement detector 11 for producing a measurement signal representing the reflected measurement beam is provided for receiving the measurement beam after it has passed through the medium M to be studied. The outputs of the reference and measurement detectors 8 and 11 respectively are connected to the electronic processing circuit 12 which is arranged to supply, from information detected by the detectors 8 and 11, data relating to the lines of the emitted beam which have undergone absorption by the medium M studied and, consequently, to the composition of the medium. A block diagram of electronic processing circuit 12 is shown in FIG. 2.

The detectors 8 and 11 must be adapted to react to the wavelength of the signals emitted by the laser 1 and to have a wide band-pass. For this purpose, there are advantageously employed detectors of types Cd Te - Hg Te of the type for example manufactured and sold by S.A.T., or alternatively Molectron pyrotechnical detectors, type P3.

As shown in FIG. 2, the electronic processing circuit 12 comprises a selector arrangement constituted by a pulse counter 13 connected to the output of the angular coder 6 and a decoder arrangement 14. The counter 13 and the angular coder may be for example of the type commercially available in the form of a single assembly manufactured and sold by the German firm HEIDENHAIN - types ROD 1/45.7 and VRZ 3002.

The output of the counter 13 is connected to the input of the decoder arrangement 14 which has 500 positions, the decoder arrangement 14 being adapted to extract from 500 positions of the counter 13 covering the useful sector of the dihedral 3 arrangement, those positions which represent best the wavelengths of the lines of the pulsed emission to be processed.

The decoder arrangement 14 has two outputs, one of which is connected to the input of square-wave pulse generator 15 for producing gating signals. The other output of the decoder 14 is connected to a logic circuit 16 constituting an interface circuit for distributing data to various output devices 32 to 35.

The generator 15 has an output connected to an input of a trigger in the form of an AND gate 17 having two inputs the other input of the gate 17 being connected to the reference detector 8 via an amplifier 18 and a comparator 19.

The output of the AND gate 17 is connected to one of the two inputs of a restoring circuit 20 for producing a signal indicating a line missing from the emission of the source 1, the other input of the circuit 20 being connected to the output of the circuit 15.

The output of the restoring circuit 20 connected to the AND gate 17 is also connected to a triggering input of an integrator 21 for integrating reference signals received from the reference detector 8 via an amplifier 18. An analogue-to-digital converter 22 is provided for producing digital signals representing the integrated reference signals. An analogue-to-digital converter 27 is provided to convert the integrated measurement signals to digital signals. The converter 27 is connected to the integrator 24 via a regulatable gain amplifier 28. Regulaton of the gain of the amplifier is effected by switching means 29 having two positions permitting a selection between two predetermined values of the gain, i.e. 1 or 10.

The other output of the restoring circuit 20 is connected to a first input of an OR gate 23 having two inputs, the second input of the OR gate being connected to an output of an integrator 24 for integrating measurement signals received from the measurement detector 11 via an amplifier 25. The integrator 24 has a triggering input connected to the output of the AND gate 17 via a regulatable delay circuit 26. The amplifiers 18 and 25 are connected to the said other output of the decoder 14 which output is for synchronisation of the operation of the amplifiers with rotation of the dihedral arrangement 3.

The output of the OR gate 23 is connected to a control input of the analogue-to-digital converter 22 and to a control input of the analogue-to-digital converter 27. The OR gate is arranged to issue orders controlling when conversion takes place.

The digital outputs of the converters 22 and 27 are connected, respectively, by multiple conductors to reference and measurement inputs of the logic circuit 16. The converters also have further outputs at which signals indicating the end of conversion are produced. These further outputs are connected, via an AND gate 30, to an end of conversion input of the logic circuit 16 and also to resetting to zero inputs of the integrators 21 and 24.

The logic circuit 16 is connected to the output devices 32 to 35. There is a predetermined number of these devices, which are for data exploitation. They comprise, by way of example a measurement data store 31, a reference data store 32, a circuit 33 for calculating the ratio M/R where M is the value of the measurement data and R the value of reference data, a tape-punch 34, and a printer 35.

Some of the circuits employed in the electronic processing circuit 12 shown in FIG. 2 will now be described in greater detail.

The angular coder and counter 6, 13, is adapted to supply twenty thousand words for one rotation of the coder 6, each word being in the form of five-digit data in binary coded decimal or BCD code.

As indicated hereinabove, with reference to the description of FIG. 2, the useful sector of the rotatable dihedral arrangement 3 is covered by the first five hundred positions of the coder 6.

Figure 4:
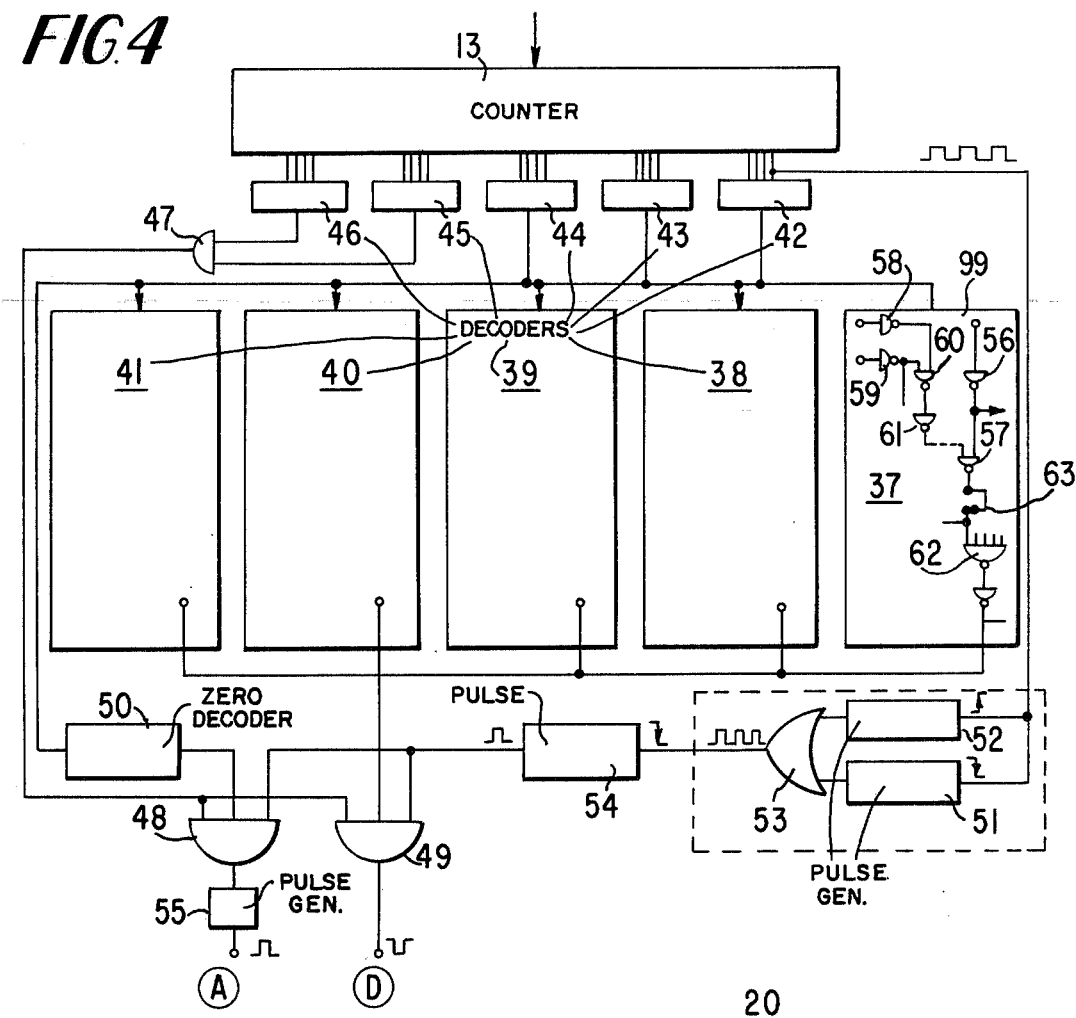
FIG. 4 is a block diagram of a decoding circuit of the processing circuit of FIG. 2.

The decoder arrangement 14, designed to extract from these positions those best representing the wavelengths of lines of light pulses to be processed, is shown in FIG. 4. It comprises five decoding circuits in the form of cards 37 to 41 each arranged to be associated with a particular set of one hundred positions. The outputs of the thousands and the tens of thousands of the counter 13 are connected via two BCD to Decimal decoders 45 and 46 for example of type SN7442 (Texas Instruments Inc.) to the two inputs of an AND gate 47 the output of which is connected to respective first inputs of two AND gates 48 and 49 each having three inputs.

A second input of the gate 48 is connected to the output of the decoders 42 and 44 through intermediary of a zero decoding circuit 50.

A second input of the gate 49 is connected to the common output of the cards 37 to 41.

The third inputs of the gates 48 and 49 are connected via a pulse generator 54 to the output of a clock. The clock comprises two pulse generators 51 and 52 the inputs of which are connected to the output having the lowest weight of the counter 13 and the outputs of which are connected to respective inputs of an OR gate 53. The output of the OR gate 53 is connected to the input of the pulse generator 54. The output of the gate 48 is connected to the logic circuit 16 of the circuit of FIG. 2 via a sync. pulse generator 55 for generating synchronisation pulses for synchronisation with the rotation of the dihedral arrangement 3. The output of the gate 49 is connected to the input of the validation signal producing circuit 15.

Each of the cards 37 to 41 is an integrated circuit arranged as an OR gate having one hundred input circuits. The cards 37 to 41 are arranged to receive, respectively, the positions 0 to 99, 100 to 199, 200 to 299, 300 to 399, and 400 to 499 of the counter 13.

The input circuits of the cards 37 to 41 are connected to the outputs 0 to 499 of the counter 13 via logical decoder circuits constituted by BCD to decimal decoders 42 to 44 of type identical to decoders 44 and 45 i.e. of, for example, the type SN 7442 manufactured by Texas Instruments Incorporated.

Each of the decoding cards 37 to 41 is arranged in ten decade circuits associated with ten decades respectively. The ten decade circuits of the card 37, (which receives the positions 0 to 99 of the counter 13) are arranged to receive the positions 0 to 9, 10 to 19, . . . 90 to 99 respectively.

Each decade circuit comprises ten input circuits, each input circuit being constituted by an inverter 56, of, for example SN 7404 type, and a positive NAND gate 57 of, for example SN 7403 type. In each input circuit the input of the inverter constitutes one input of the decade and the output of the inverter is connected to one of two inputs of the positive NAND gate 57. The other input of the gate 57 of each input circuit is connected to a common weighting circuit for determining the weight of the digits counted by the decade circuit.

The weighting circuit of each decade circuit comprises an inverter 58 of, for example SN 7404 type, and a positive NAND gate 60 (of, for example type SN 7400). The input of the inverters 58 of the weighting circuits are connected to the respective tens outputs of the counter 13. The output of each inverter 58 is one of the two inputs of the NAND gate 60, of for example SN 7400 type, the output of which is connected to the inputs of all the gates 57 of the decade circuit, via a common inverter 61, of for example type SN 7404. The other input of each gate 60 of the ten weighting circuits of the card 37 is connected to the output of a common Positive NAND gate 59, the input of which is connected to the 0 hundreds output of the counter 13.

The weighting circuit associated with the decade circuit for counting the positions from 10 to 19 is identical with the weighting circuit associated with the decade circuit for counting 0-9, but its input is connected to the 1 tens output of the counter 13. In summary the card 37 comprises one hundred input circuits 56, 57 and ten weighting circuits such as 58, 60, 61, the gate 59 being common to all the decade circuits of the card 37.

The other cards are identical to the card 37.

The output of the gate 57 is connected to an input of a plurality of OR gates connected in parallel and represented on the card 37 by an OR gate 62. Connecting riders, or sliders 63 are connected between the outputs of the respective NAND gates 57 and the respective inputs of the OR gate 62 in such manner as to make it possible to neutralise, if desired (simply by removing at least one of the sliders 63) at least one of the corresponding positions of the coder 6.

Preferably Positive NAND gates are used to implement the OR gate 62. These NAND gates may be of, for example, the type SN7430. All the gates of type SN 74' mentioned hereinabove are manufactured by Texas Instruments Incorporated.

Figure 5:
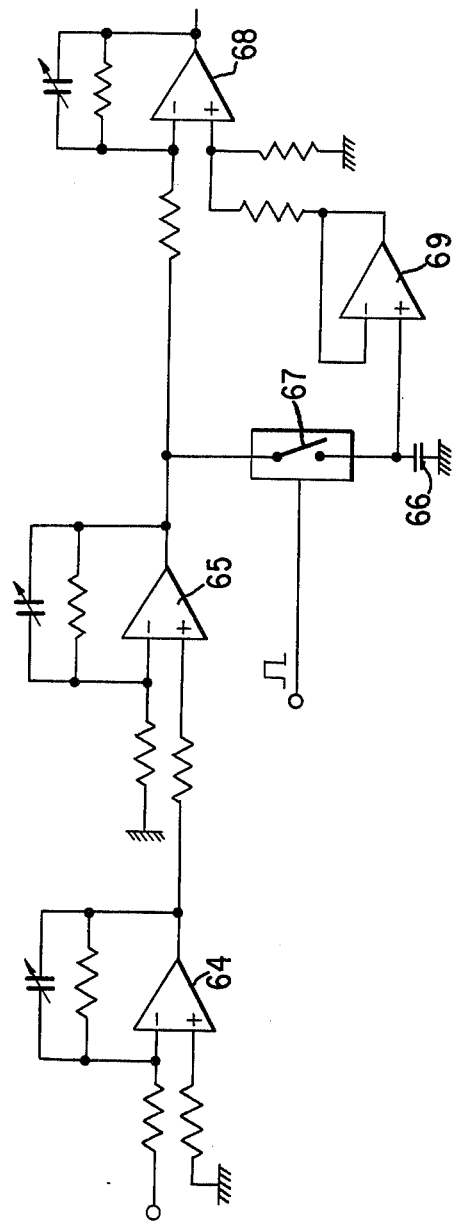
FIG. 5 is a circuit diagram of measurement and reference amplifiers of the processing circuit of FIG. 2.

Both the reference and measurement amplifiers 18 and 25 of the circuit of FIG. 2 may be implemented as shown in FIG. 5.

The amplifier shown in FIG. 5 comprises, the series arrangement of an inverting amplifier 64 and a noninverting amplifier 65.

The output of the series arrangement has a drift which is not negligible and which may impair the functioning of the circuits with which the amplifiers 18 and 25 are connected. In particular, the functioning of the comparator 19 connected to the output of the reference amplifier 18 may be impaired.

In order to nullify the drift, a capacitor 66 is connected to the output of the amplifier 65 via a controllable switch 67, (e.g. a circuit breaker of type DG 133 BP, manufactured by Siliconix,) and to earth. The switch 67 is connected to be controlled by square-wave signals obtained from the synchronisation output, of the decoder 14 for synchronisation of operation of the switch 67 with the rotation of the dihedral arrangement 3.

The junction point between the capacitor 66 and the switch 67 is connected to one of two inputs of a unity gain correction amplifier 68 via a voltage follower 69.

The other input of the correction amplifier 68 is connected to the output of the amplifier 65. The synchronisation pulse in respect of rotation of the dihedral arrangement 3 corresponding to decoding zero of the decoder arrangement 14 (FIG. 2) appears before any pulse of a line and permits storing in the capacitor 66 the base line voltage of the train of pulses associated with the drift.

This voltage is integrally taken from the signal to be processed by the correction amplifier 68 during the periods of passage of the signals to be measured.

The amplifiers used in implementing amplifiers 18 and 25 may advantageously be circuits such as are produced and sold by Analog Devices, of type 149A in respect of amplifiers 64, 65 and 68 and of type ADP 511 C in respect of the voltage follower 69.

Figure 6:
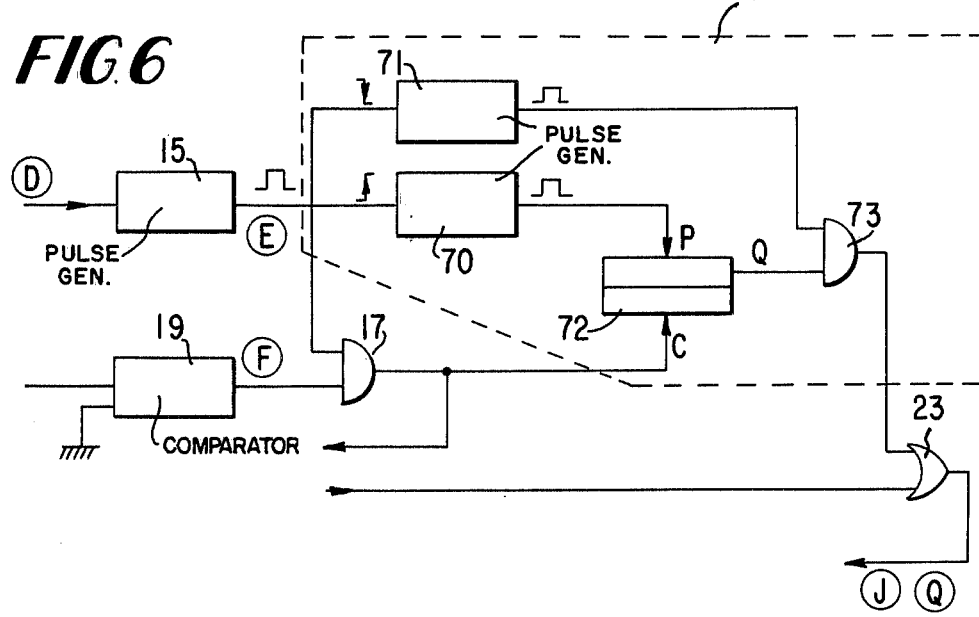
FIG. 6 is a block diagram of a restoring circuit of the processing circuit of FIG. 2.

The restoring circuit 20 of the circuit shown in FIG. 2 is shown in FIG. 6.

The inputs of the restoring circuit 20 are constituted by the generator 15 and the comparator 19 which are connected to the AND gate 17 (FIG. 29. The restoring circuit 20 comprises two pulse generators 70 and 71, which are responsive to the leading and trailing edges, respectively, of the output signal of the circuit 15, a Flip-Flop 72, and an AND gate 73.

The pulse generator 70 is connected to the present input P of the flip-flop 72, the clear input C of the flip-flop being connected to the output of the AND gate 17. The output Q of the flip-flop is connected to one of the two inputs of the AND gate 73. The other input of the AND gate 73 is connected to the output of the pulse generator 71. The output of the AND gate 73 is connected to one of the inputs of the OR gate 23 (FIG. 2) the other input of which is connected to the end of integration output of the measurement integrator 24 (FIG. 2).

The leading edge of each gating signal (square-voltage pulse) issuing from the generator 15 triggers the generator 70 which opens the AND gate 73. If emission from the laser 1 takes place with the production of the gating pulse, the comparator 19 detects whether or not there is produced a line to be studied, and if there is the AND gate 17 supplies an integration order whilst simultaneously causing closing of the AND gate 73.

If there has been no emission of the line under consideration, the comparator 19 remains inoperative. The integrators 21 and 24 (FIG. 2) are not triggered, but the AND gate 73 which has been opened by the leading edge of the authenticating gating pulse from the circuit 15 permits passage of the pulse supplied by the generator 71, and triggered by the trailing edge of the authenticating gating pulse.

Thus, the converters 22 and 27 (FIG. 2) supply value zero for any missing line, thereby avoiding shifting of the numerical values which have been stored.

The pulse generators utilised in the restoring circuit shown in FIG. 6 may advantageously be monostable multivibrators of for example type SN 74121, the flip-flop 72 is a J-K Master Slave Flip-flop of an SN 7476 type for example, the AND gate 73 may comprise a Positive NAND gate SN 7400 type, all these circuits being manufactured and sold by Texas Instruments Incorporated. The comparator 19 may be a circuit produced by R.C.A. comprising a uA 710 comparator and a uA 741 amplifier.

An integrator which may be used as reference integrator 18 and also as measurement integrator 25 in the circuit shown in FIG. 2 is shown in FIG. 7. It comprises a monostable circuit 74, for regulating the integration period; which may be a monostable of type SN 74121 for example. The input 75 of the monostable 74 constitutes the integration triggering input and an output 76 of the monostable 74 constitutes the integration gating pulse output, this output being furthermore connected to a J-K Master-slave flip-flop 77 which may be of type SN 7476 for example. The flip-flop 77 has a further input 78 for resetting the integrator to zero.

The monostable 74 has a further output connected to an analog gate 79 via an amplifier 80. The output of the gate 79 is connected to one of two inputs of an integrating amplifier 81 the other input of which is connected to a shift control circuit 82.

The amplifier 81 may advantageously be an amplifier of type ADP 511 C produced by Analog Devices.

The output of the flip-flop 77 is connected via a diode 83 and an NPN transistor 84 to one of two inputs of a further analog gate 85, the other input of which is connected to the output of the amplifier 81, the output of the amplifier 81 being connected to the output of the gate 79 also.

The gates 79 and 85 may be, for example CD 4016 circuits produced by R.C.A.

The analysis device described hereinabove is adapted to operate in the following manner:

The embodiment of the laser 1 shown in FIG. 1 is permanently excited in such manner that it functions continuously. The dihedral arrangement 3 rotates rapidly about the axis constituted by the junction of the grid 4 and of the mirror 5, and the orientation thereof is detected at each instant by the angular coder 6.

For a predetermined number of angular orientations of the dihedral arrangement 3 relative to the optical axis of the laser 1, the laser 1 emits. At each predetermined orientation a laser beam of a predetermined wavelength is transmitted from the grid 4. The result thereof is that during each rotation of the dihedral arrangement, the laser 1 emits a series of pulses of different wavelengths.

The laser beam emitted remains fixed during rotation of the dihedral.

If a laser, such as a liquid laser, which emits pulses of bands of wavelengths, and/or pumping is pulsed, the pumping and operatic of the laser is synchronised with rotation of the grid.

The separator 7 extracts a portion of the beam and directs it towards the reference detector 8. The other portion of the laser beam is collimated by the collimator 9, passes through the medium M of which it is desired to establish the spectrum, and is then reflected by the reflector 10 and returned to the separator 7, passing once again through the medium M and the collimator 9. The separator 7 transmits a portion of the reflected beam on to the measurement detector 11.

The signals received by the detectors 8 and 11 and also those from the angular coder 6 are applied to the electronic processing circuit 12 which determines the absorption of the medium M on a predetermined number of selected wavelengths.

The mode of functioning of the electronic processing circuit 12 (which is shown in greater detail in FIGS. 2 and 4 to 7), will now be described with additional reference to the signal amplitude-time diagrams of FIG. 3.

It is the purpose of the processing circuit 12 to amplify and then to quantify the pulses emitted by the reference detector 8 and the measurement detector 11, which receives respectively, the light pulses emitted by the laser 1 and the dihedral arrangement 3, and the light pulses reflected by the reflector 10 which have twice passed through the medium M to be studied (FIG. 1).

The circuit 12 also provides synchronisation of the quantification and restores data relating to the composition of the spectrum of the medium studied such as might readily be exploited on a printer or a tape perforator.

The principle of the processing is to integrate the pulses relating to the emission and reception lines during the same period starting from the leading edge of the pulses, and then to convert the analogue integration voltage obtained to numerical data.

With the laser 1 functioning and subsequent to a starting order signal which may be generated by a manually operated means, acquisition of the information necessary for the data commences as soon as the dihedral arrangement is in a predetermined datum position at which the coder 6 supplies to the decoder 14 a signal which the decoder 14 converts to a rotation synchronisation signal A which it applies to the distribution logic circuit 16 and also to the reference and measurement amplifiers 18 and 25, for the purpose of correcting the drift of their outputs (as described with reference to FIG. 5.)

Figure 3:
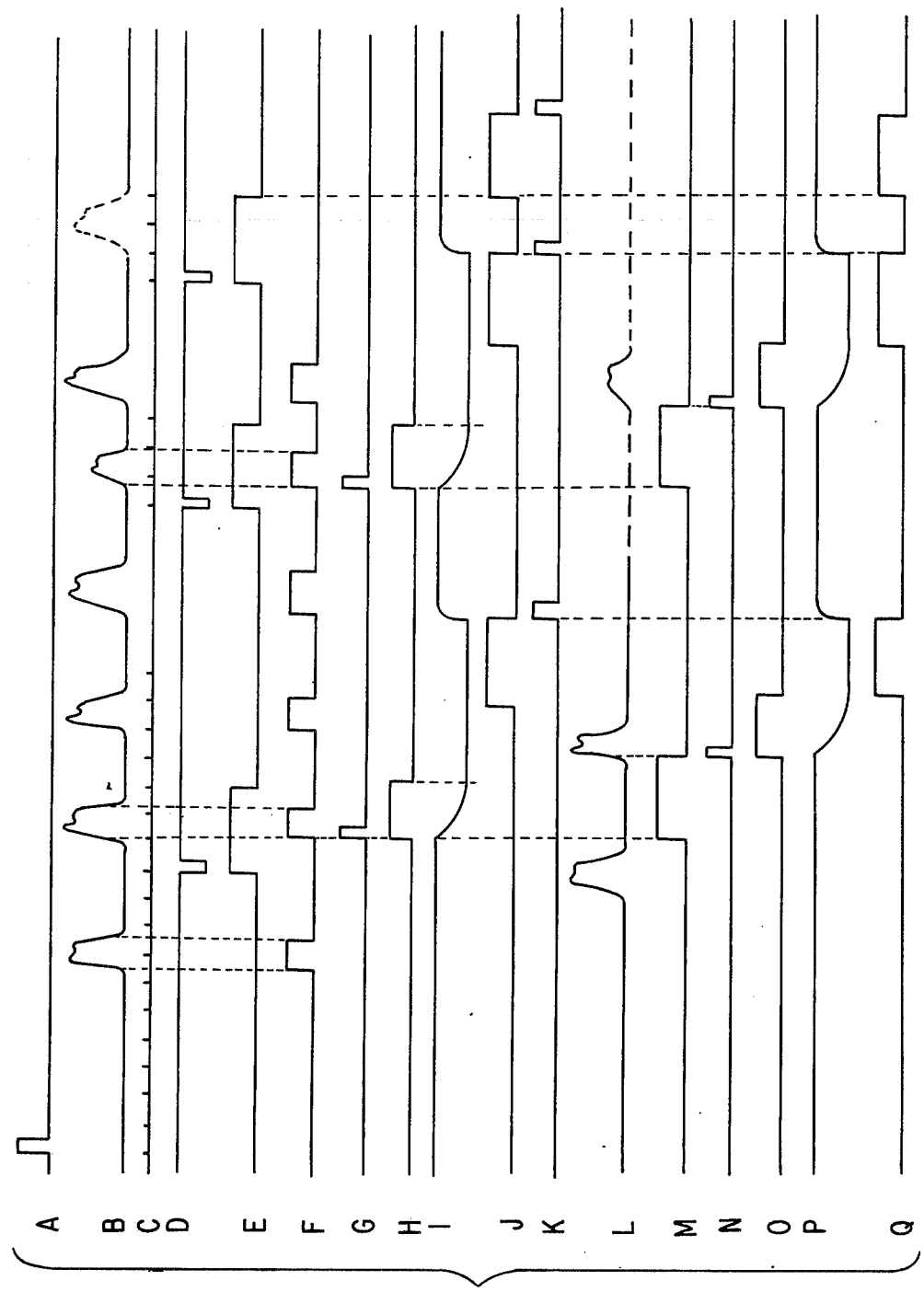
FIG. 3 shows signal-amplitude-time diagrams of signals which may occur in operation of the processing circuit of FIG. 2.

This signal A is shown by the graph A in FIG. 3.

Before the generation of a starting order signal, the decoder arrangement 14 (a more detailed circuit diagram of which is given in FIG. 4), is programmed by disposing on the cards 37 to 41 riders 63, in such manner as to select the best positions of the dihedral arrangement to serve as origins for the processing of predetermined lines of the detected spectrum. Generally, the positions immediately preceding the leading edges of the pulses to be processed are selected.

The decoder thus programmed decodes only predetermined positions of the first five hundred positions covering the emission zone or range, from among the twenty thousand positions supplies by the coder 6 (graph C in FIG. 3).

Each time that the decoder 14 receives from the coder 6 a pulse corresponding to a selected line, it applies a line synchronisation output pulse or indicator signal D (graph D in FIG. 3) to the generator 15 which supplies a gating signal E (graph E in FIG. 3) to the AND gate 17 and to the restoring circuit 20.

Simultaneously, the reference detector 8 (FIG. 1) applies to the reference amplifier 18 a reference signal B representing the line of the spectrum to be studied and resulting from that portion of the light beam which the separator 7 has directed towards the detector 8. These signals B are shown by diagrams B of FIG. 3.

The output signals of the amplifier 18 are applied to the comparator 19 which compares their amplitude with a reference value.

If the signal obtained from the amplifier 18 has sufficient amplitude, the comparator supplies an output comparison signal F (diagram F in FIG. 3) to the AND gate 17.

In the event of simultaneous presence of the gating signal and the comparison signal supplied by the circuit 15 and the comparator 19 to the inputs of the AND gate 17, it emits an integration order control signal G (diagram G in FIG. 3) which is applied to the reference integrator 21 which commences integration of the signals derived from the amplifier 18. The integration duration is determined by the duration of the gating pulse E supplied by the generator 15 starting from that instant at which the integration order control signal G is generated by the gate 17.

The integration duration is represented by diagram H in FIG. 3, whereas the output signal I of the integrator 21 is represented by the diagram I.

The measurement signal transmitted to the measurement amplifier 25 by the measurement detector 11 reaches the electronic processing circuit 12 with a predetermined delay relative to the associated reference signal, due to the propagation time required by the transmitted light pulse to pass through the medium M to be studied. (This delay is illustrated in diagram L).

In order that the measurement integrator 24 may be triggered at the instant at which the measurement signal is applied to it, the integration order control signal G emitted by the AND gate 17 is supplied to it via the regulatable delay dircuit 26. (This delay is illustrated in diagram M). The trailing (in this case descending) edge of the signal produced by the delay circuit constitutes the integration order signal N for the measurement integrator 24 (diagram N), the integration period signal of the reference integrator but phase shifted relative thereto.

At the end of the integration operation effected by the measurement integrator 24 a diagrammatic representation of the output of integrator 24 is shown in diagram P), it applies to the A to D converters 22 and 27 respective conversion order signals J, Q, via the OR gate 23. (The conversion order signals are shown in diagrams J and Q).

The converters 22 and 27 convert, respectively, the analogue integrated reference and measurement voltages to numerical data, and supply the numerical data to the distrubution logic system 16. The converters 22 and 27 operate simultaneously.

On completion of conversion, the converters 22 and 27 supply output signals to the AND gate 30 which applies a reset to zero signal K to the integrators 21 and 24 and an end of conversion signal K to the logic circuit 16 (diagram K).

The logic circuit 16 stores in the reference store 35 and in the measurement store 34 the output data of the converters 22 and 27 in the order of presentation of the data. The ratio M/R is calculated in the circuit 33. The data is also transferred to the printer 32 and to the tape punch 31. the data thus processed may be exploited on a computer. If, for any reason whatsoever, a line to be processed (shown in dotted line on the graph B of FIG. 3) is missing in the emission, the end of the gating pulse E produced by the generator 15 brings about triggering of the converters 22 and 27 by means of the restoring circuit 20 which produces a signal indicating a missing line and via the OR gate 23.

The result of such a conversion is zero, since the integrators 21 and 24 have not functioned. This makes it possible to preserve the word (or order) associated with each line during the subsequent processing and storing of the numerical data.

In the electronic processing circuit shown in FIG. 2, integrators 21 and 24 are utilised, but it is self-evident that the said integrators could be replaced by peak detectors for the reference and meansurement signals. The integrators or peak detectors constitute data producing circuits for producing analogue signals representing data relating to spectroscopic analysis of the medium M.

It is also possible to connect the outputs of the converters 22 and 27 directly to a computer which, after processing the data, would supply directly data relating to the composition of the medium M studied.

The data supplied by the printer 32 may be directly exploited by direct read-out.

If the laser is pulse operated pumping of it should be synchronised with the change of grid position, and processing of the data may then be effected in a manner similar to that described hereinabove whilst providing for frequency interruption of the signals by electronic means from known positions of the grid.

The analysis device described hereinabove by way of example makes it possible to very rapidly determine the composition of a medium of considerable thickness by spectroscopic analysis, without sampling and without localisation. The device can be used for studying zones of the atmosphere with a view to combatting atmospheric pollution for example.

What is claimed is:

1. Apparatus for the spectroscopic analysis of a sample of material for determining the chemical composition of the sample, the apparatus comprising:
    a coherent radiation source for producing, in succession, respective ones of a plurality of different wavelengths of the coherent radiation, the source having an active material from which there can be produced the said different wavelengths of coherent radiation, reflecting means for reflecting radiation in the source, and
    a wavelength selecting means operable by variation of its angular orientation relative to the axis of propagation of coherent radiation in the source to sequentially select respective ones of the different wavelengths;
    a separator for separating the radiation into a measurement portion for irradiating a sample of material and a reference portion;
    a reference detector arranged to receive the reference portion and to produce a reference signal representing the reference portion;
    a measurement detector arranged to receive the radiation from the sample of material due to the irradiation of the sample by the measurement portion and to produce a measurement signal representing the said radiation from the sample; and
    a processing circuit for processing the reference and measurement signals in dependence upon variation of the said angular orientation of the selecting means to produce numerical data relating to the spectral analysis of the sample;
    said processing circuit comprising:
    an angular position detecting means for producing position signals representing the angular orientations of the selecting means relative to the said axis of progation:
    a selector arrangement connected to receive the position signals for producing indicator signals indicating a particular orientation of the selecting means, and thus the production of a particular wavelength of radiation, and indicating that the reference and measurement signals associated with that orientation are to be processed by the processing circuit;
    a comparator connected to receive the reference signals and operable to produce a comparison signal indicating the presence of a reference signal;
    first and second, controllable data producing circuits connected to receive the reference and measurement signals respectively to produce analogue signals representing data relating to the spectroscopic analysis of the sample;
    a trigger arranged to produce, in dependence upon the comparison signal and the indicator signal, a control signal for the data producing circuits;
    first and second analogue to digital converters connected to receive the analogue signals from the first and second data producing circuits respectively; and
    an interface circuit connected to receive the said data from the converters.

2. Apparatus as recited in claim 1, additionally comprising a measurement portion reflector arranged at a predetermined distance from the separator to reflect the measurement portion back to the measurement detector, the said radiation from the sample being the reflected measurement portion.

3. Apparatus as recited in claim 2, wherein said reflecting means is substantially totally reflective, and the selecting means comprises a dihedral arrangement of a diffraction grating and a plane reflector, the dihedral arrangement being pivotable about an axis coaxial with the intersection of the planes of the grating and said plane reflector.

4. Apparatus as recited in claim 2, wherein the selecting means comprises another reflector spaced from said reflecting means, and a prism rotatably arranged in the space between said reflecting means and said another reflector.

5. Apparatus as recited in claim 2, wherein the selecting means comprises a further reflector spaced from said reflecting means, and a rotatable Fabry-Perot system arranged in the space between said reflector and said another reflector.

6. Apparatus as recited in claim 1, wherein the reflecting means is partially transparent and the selecting means comprises a pivotably arranged diffraction grating, emission of radiation being effected through the said reflecting means.

7. Apparatus as recited in claim 1, wherein the angular positon detecting means comprises an angular coder operable to produce digital position signals representing the angular orientations of the selecting means.

8. Apparatus as recited in claim 7, wherein the selector arrangement comprises a counter, connected to receive the digital position signals, for counting the angular orientations of the selecting means, and a decoder arrangement for selecting those angular positions corresponding to the respective ones of the plurality of wavelengths and for selecting at which of those orientations an indicator signal will be produced.

9. Apparatus as recited in claim 8, wherein the decoder arrangement is pre-programmable to select the angular orientations.

10. Apparatus as recited in claim 1, wherein the selector arrangement comprises:
a counter for counting angular orientations of the selecting means;
logical decoder circuits connected to decode signals from the counter representing a predetermined number of angular orientations of the selecting means at which coherent radiation could be produced from the source;
and a plurality of decoding circuits connected to the logical decoder circuits, the decoding circuits constituting logical OR gates having a total number of input circuits equal to the said predetermined number of angular orientations, the input circuits incorporating respective control arrangements whereby they can be manually rendered operative or inoperative in order to program the selector arrangement to select certain ones of the angular orientations.

11. Apparatus as recited in claim 10, wherein each control arrangement is constituted by spaced apart end portions of two conductors adapted to be bridged by a further conductor to render the associated input circuit operative.

12. Apparatus as recited in claim 10, further comprising synchronisation signal producing means for producing, from signals produced by the counter, a synchronisation signal for synchronising the operation of the processing circuit with the variation of angular orientation of the selecting means and for producing, from signals produced by the counter and by operative ones of the said input circuits, the said indicator signals.

13. Apparatus as recited in claim 1, comprising a delay circuit, wherein the second data producing circuit is connected to receive the control signal from the trigger via the delay circuit.

14. Apparatus as recited in claim 13, wherein each data producing circuit comprises an integrator.

15. Apparatus as recited in claim 1, wherein each dta producing circuit comprises a peak detector.

16. Apparatus as recited in claim 12, comprising amplifiers respectively connected to receive the reference and measurement signals and to feed them to the respective first and second data producing circuits, each amplifier comprising drift control means, for controlling drift of the output of the amplifier, the drift control means being arranged to be triggered by the said synchronisation signal.

17. Apparatus as recited in claim 16, wherein each data producing circuit comprises an integrator, the integrator comprising:

a monostable for regulating the integration period, having an input connected to receive the control signal from the trigger and two outputs;
an analogue gate an input of which is connected to one of the outputs of the monostable; an integration amplifier having two inputs one of which is connected to the output of the analogue gate;
a shift control circuit connected to the other input of the integration amplifier;
a flip-flop for resetting the integrator to zero having an input connected to the other output of the monostable and another input for receiving a reset to zero signal; and
a further analogue gate having an output connected to the said one input of the integration amplifier, and having inputs connected to the output of the flip-flop and to the output of the integration amplifier respectively.

18. Apparatus as recited in claim 1, wherein each analogue to digital converter comprises an output for producing a signal indicating the end of a conversion period, and wherein each of the data producing circuits comprises an input for receiving a reset to zero signal for resetting the data producing circuit, the apparatus further comprising an AND gate for receiving the signals from the converters indicating end of a conversion period and for producing therefrom the reset to zero signal for resetting the data producing circuits.

19. Apparatus as recited in claim 1, wherein the analogue to digital converters are operable in dependence, upon the production of a cmparison signal, the apparatus further comprising a restoring circuit for producing a conversion rigger signal for triggering the digital to analogue converters to operate when an indicator signal has been produced by the selector arrangement and no comparison signal has been produced.

20. Apparatus as recited in claim 19, further comprising a pulse generator for converting the indicator signal to a square-wave gating signal the restoring circuit comprising:
first and second pulse generators respectively adapted to be triggered by the leading and trailing edges of the square-wave pulse;
a flip-flop having a preset input connected to the output of the first pulse generator and a clear input connected to the output of the said trigger which is connected to receive the comparison signal and the square-wave pulse;
an AND gate, having a first input connected to the output of the second pulse generator and a second input connected to an output of the flip-flop, for producing the said conversion trigger signal.

21. Apparatus as recited in claim 20, further comprising an OR gate connected to receive the conversion trigger signal and to control the converters.

22. Apparatus as recited in claim 1, further comprising a store for storing measurement data;
a store for storing reference data;
calculating means for calculating the ratio of the value of measurement data to the value of reference data; and
data read-out means;
the stores, calculating means and data read-out means being connected to receive data from the interface circuit.

23. Apparatus as recited in claim 1, wherein the source comprises a laser having a gaseous or liquid active material.

* * * * *